United States Patent [19]
Williams et al.

[11] Patent Number: 5,616,369
[45] Date of Patent: Apr. 1, 1997

[54] PROCESS FOR BARRIER COATING OF PLASTIC OBJECTS

[75] Inventors: Joel L. Williams, Cary; Susan L. Burkett, Hillsborough, both of N.C.; Shel McGuire, Omaha, Nebr.

[73] Assignee: Becton, Dickinson and Company, Franklin Lakes, N.J.

[21] Appl. No.: 265,173

[22] Filed: Jun. 24, 1994

Related U.S. Application Data

[63] Continuation-in-part of Ser. No. 125,704, Sep. 23, 1993, Pat. No. 5,364,666.

[51] Int. Cl.$^6$ ..................... H05H 1/00
[52] U.S. Cl. ............. 427/536; 427/255.3; 427/255.7; 427/294; 427/299; 427/348; 427/350; 427/539; 427/560; 427/563; 427/571; 427/574; 427/579; 427/600
[58] Field of Search ........................ 427/535, 600, 427/539, 560, 563, 536, 571, 574, 579, 255.3, 255.7, 294, 299, 350, 348

[56] References Cited

U.S. PATENT DOCUMENTS

| | | | |
|---|---|---|---|
| 3,733,309 | 5/1973 | Wyeth et al. | 260/75 |
| 4,552,791 | 11/1985 | Hahn | 428/35 |
| 4,557,946 | 12/1985 | Sacher et al. | 427/41 |
| 4,599,678 | 7/1986 | Wertheimer et al. | 361/323 |
| 4,815,962 | 3/1989 | Cardone | 427/38 |
| 4,992,298 | 2/1991 | Deutchman et al. | 427/38 |
| 5,053,244 | 1/1991 | Kieser et al. | 427/38 |
| 5,055,318 | 10/1991 | Deutchman et al. | 427/38 |
| 5,364,666 | 11/1994 | Williams et al. | 427/255.3 |

FOREIGN PATENT DOCUMENTS 0299754  7/1987  European Pat. Off. ........ C23C 16/40

OTHER PUBLICATIONS

A. Sharma and H. Yasuda, "Plasma Polymerization of Tetramethyldisloxane by a Magnetron Glow Discharge", Sep. 22, 1983.

N. Morosoff, W. Newton and H. Yasuda, "Plasma Polymerization of Ethylene by Magnetron Discharge", Jul. 31, 1978.

M. Leahy and G. Kaganowicz, "Magnetically Enhanced Plasma Deposition and Etching", Apr. 1987.

Primary Examiner—Bernard Pianalto
Attorney, Agent, or Firm—Nanette S. Thomas

[57] ABSTRACT

A method for sequentially depositing a silicon oxide based film as a barrier on a substrate. The film is useful for providing an effective barrier against gas permeability in containers and for extending shelf-life of containers, especially plastic evacuated blood collection devices.

20 Claims, 4 Drawing Sheets

PROCESS FOR BARRIER COATING OF PLASTIC OBJECTS

This application is a continuation-in-part of U.S. Ser. No. 08/125,704, filed on Sep. 23, 1993, U.S. Pat. No. 5,364,666.

BACKGROUND OF THE INVENTION

1. Field of the Invention

This invention relates to a method for depositing a barrier coating to plastic containers for improving the effective barrier of the plastic container against gas and water permeability.

2. Description of the Related Art

In numerous fields of technology, it is necessary to apply very thin coatings of pure substances to certain objects. An example is window glass which is provided with a thin coating of metal oxide in order to filter certain wavelength ranges out of sunlight. In semi-conductor technology, thin coatings of one or more substances are often applied to a substrate. It is especially important that the thin coatings not only be pure, but also that they be precisely measured out so that the coating thickness and, in the case of coatings of chemical compounds, their composition will be accurately repeatable. These coating thicknesses are, as a rule, between two and several thousands of nanometers.

A variety of methods are known for applying thin coatings to films, glass and other substrates. Such processes for depositing $SiO_x$ onto plastic objects are disclosed in U.S. Pat. No. 5,053,244 and European Pat. No. 0 299 754. Most specifically, these processes can provide excellent barrier properties to plastic ms which have not been exposed to dust. However, these processes provide only minor barrier properties to three-dimensional plastic objects or films that are exposed to dust.

It is believed that the inability to obtain a good barrier on three-dimensional plastic objects is due to the lack of cleanliness of the object's surface since most three dimension objects are exposed to dust during fabrication.

In the process of depositing $SiO_x$ on thin films, the $SiO_x$ barrier coating is applied under vacuum conditions to a clean film. Typically, film is extruded under very clean conditions and immediately wound into a large roll. As a consequence, the film surfaces, with the exception of the outside layer, are never exposed to particles in air such as dust.

It is believed that the reason for the lack or minimum improvement in permeability of three-dimensional objects coated with $SiO_x$ is that the surface of the three-dimensional object has a contaminated surface. It is further believed that the contamination is due to foreign surface particles that settle on the object due to its exposure to air.

Even though $SiO_x$ is evenly deposited on the surface of an object at about 500 to 1000 Å in thickness, because foreign surface particles, that are on the order of 5000 to 5000 Å in diameter and may be on the surface of the object, portions of the surface are not coated with the $SiO_x$ because of the shielding effect caused by the foreign surface particles.

Therefore, a need exists to remove and/or redistribute contamination from the surface of objects that are to be coated with $SiO_x$ to improve the process for applying $SiO_x$ to the objects and more particularly, to improve the barrier properties of the objects.

SUMMARY OF THE INVENTION

The present invention is a process for sequentially depositing a barrier composition over the outer surface of an article, such as a composite container.

Preferably, the barrier composition is a silicon oxide based film. Such a film desirably is derived from volatile organosilicon compounds or gases.

Most preferably, the method for sequentially depositing a silicon oxide based film on an article, such as a plastic collection tube comprises the following steps:

(a) controllably flowing a gas stream including an organosilicon compound into a plasma;

(b) depositing a first silicon oxide based film onto the surface of the article while maintaining a pressure of less than about 100 microns Hg during the depositing;

(c) removing and/or redistributing foreign surface particles from the surface of the article; and (d) depositing a second silicon oxide based film onto the surface of the article over the first silicon based film by repeating steps (a) through (b) above.

The organosilicon compound is preferably combined with oxygen and helium and at least a portion of the plasma is preferably magnetically confined adjacent to the article during the depositing, most preferably by an unbalanced magnetron.

Preferably, the foreign surface particles are removed and/or redistributed from the surface of the article by ultrasonic vibrations or wiping. Most preferably the foreign surface particles are removed and/or redistributed with pressurized gas.

The method may also have a pre-treatment step wherein the uncoated article is exposed to a first plasma coating of oxygen, hydrogen, air or water vapor, followed by sequentially depositing silicon oxide film on the first plasma coating. Most preferably, the first plasma coating is oxygen. It is believed that the pre-treatment provides for improved adherence qualifies between the primary coating of silicon oxide and the article.

Preferably, the film provides a transparent, translucent or colorless appearance and may have printed matter applied thereon.

Alternatively, the process of depositing a silicon oxide based film can be accomplished by evaporating or sputtering a metal or metal oxide instead of plasma.

The advantage achieved by the process of sequentially depositing a silicon oxide based film with the intermittent removal and/or redistribution of foreign surface particles from the surface of the article is that improved permeability is observed.

A further advantage is that the process of the present invention improves the permeability of three-dimensional objects that has not been achieved with conventional deposition processes typically used with thin rams.

A significant advantage of the process of the present invention is that the intermittent step of removing and/or redistributing foreign surface particles on the surface of the article exposes the regions shielded by the foreign surface particles for the depositing of a second $SiO_x$ coating. Therefore, a significant reduction in permeability of the article is due to the complete $SiO_x$ surface coverage that is obtained by the sequential deposition technique and intermittent step of removing and/or redistributing the foreign surface particles.

DETAILED DESCRIPTION

Figure 1:
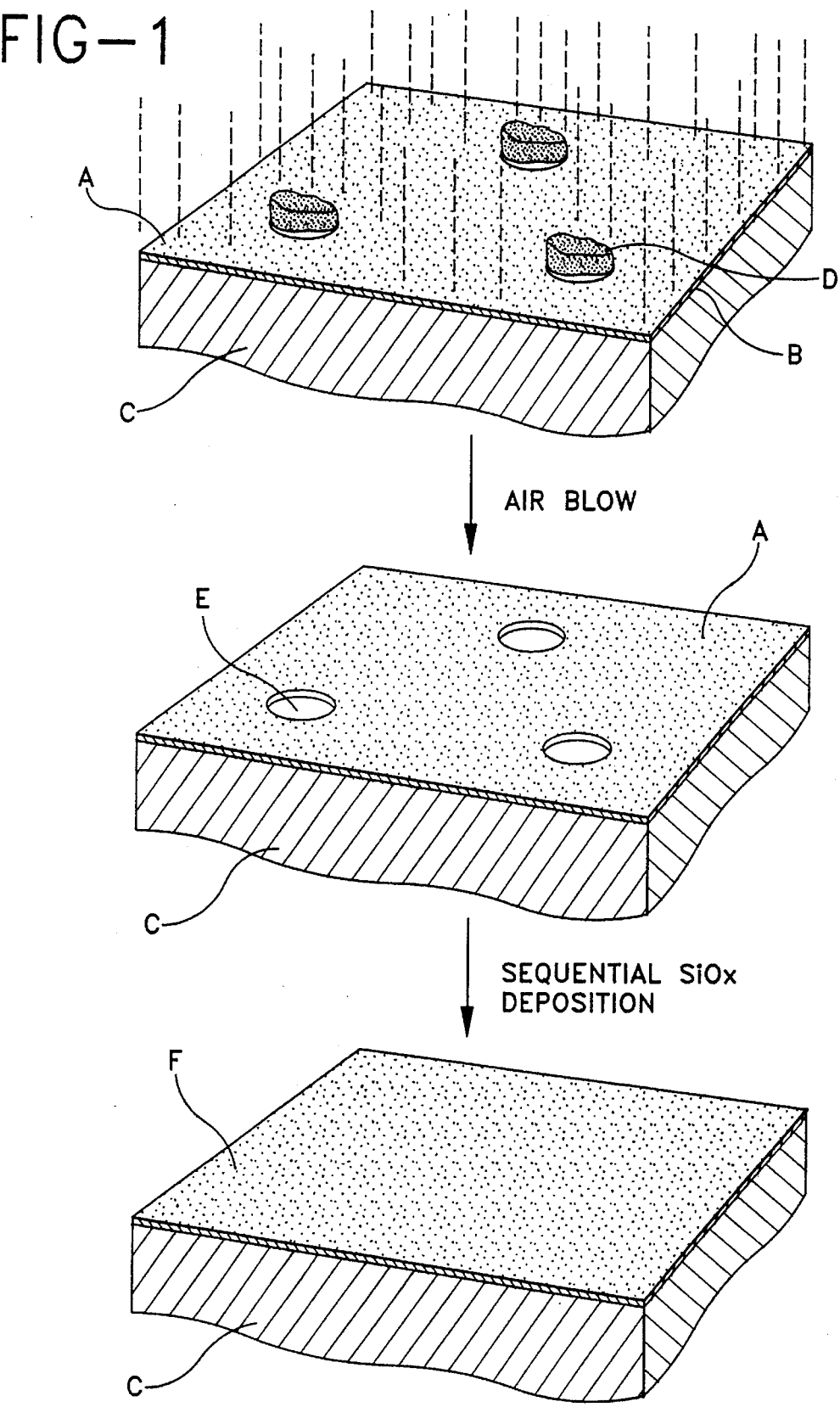
FIG. 1 is a general schematic diagram illustrating the sequential depositing of $SiO_x$.

The present invention may be embodied in other specific forms and is not limited to any specific embodiment described in detail which is merely exemplary. Various other modifications will be apparent to and readily made by those skilled in the art without departing from the scope and spirit of the invention. The scope of the invention will be measured by the appended claims and their equivalents.

The method for sequentially depositing a silicon oxide based film on a substrate is preferably conducted in a previously evacuated chamber of glow discharge from a gas stream. The gas stream preferably comprises at least three components: a volatilized organosilicon component, an oxidizer component such as oxygen and an inert gas component.

Suitable organosilicon compounds for the gas stream are liquid at about ambient temperature and when volatilized have a boiling point above about ambient temperature and include methylsilane, dimethysilane, trimethylsilane, diethylsilane, propylsilane, phenylsilane, hexamethyldisilane, 1,1,2,2-tetramethyl disilane, bis (trimethylsilane) methane, bis (dimethylsilyl) methane, hexamethyldisiloxane, vinyl trimethoxy silane, vinyl triethyoxy silane, ethylmethoxy silane, ethyltri methoxy silane, divinyltetramethyldisiloxane, divinylhexamethyltrisiloxane, and trivinylpentamethyltrisiloxazane.

Among the preferred organosilicons are 1,1,3,3-tetramethyldisiloxane, hexamethyldisiloxane, vinyltrimethylsilane, methyltrimethoxysilane, vinyltrimethoxysilane and hexamethyldisilazane. These preferred organosilicon compounds have boiling points of 71° C., 101° C., 55.5° C., 102° C., 123° C. and 127° C. respectively.

The inert gas of the gas stream preferably is helium or argon. Most preferably the inert gas is helium.

The volatilized organosilicon component is preferably admixed with the oxygen component and the inert gas component before being flowed into the chamber. The quantities of these gases being so admixed are controlled by flow controllers so as to adjustably control the flow rate ratio of the gas stream components.

The organosilicon compound and oxygen of the gas stream during the depositing are preferably in a flow rate ratio between about 1.2:1 to about 1:1.8. When the inert gas is helium or argon, then the preferred flow rate ratio of organosilicon compound, oxygen and inert gas is about 1 to 1.8:1.5 to 1.8 to 2.3.

In addition to the necessary organosilicon, oxygen and inert gas in the gas stream, minor amounts (not greater than about 1:1 with respect to the organosilicon, more preferably about 0.4 to 1.1:1 with respect to the organosilicon) of one or more additional compounds in gaseous form may be included for particular desired properties. These additional compounds include, but are not limited to a lower hydrocarbon such as propylene, methane or acetylene, or nitrogen. In particular, nitrogen increases the deposition rate, improves the transmission and reflection optical properties on glass, and varies the index of refraction in response to varied amounts of $N_2$. The addition of nitrous oxide to the gas stream increases the deposition rate and improves the optical properties, but tends to decrease the film hardness.

A particularly preferred gas stream composition has 20 to 40 SCCM organosilicon, 20 to 40 SCCM $O_2$, 40 to 60 SCCM He, 1 to 10 SCCM propylene and 5 to 20 SCCM $N_2$.

A glow discharge plasma is established in the previously evacuated chamber which is derived from one or more of the gas stream components, and preferably is derived from the gas stream itself. The article is positioned in the plasma, preferably adjacent the confined plasma, and the gas stream is controllably flowed into the plasma. A first silicon oxide based film is deposited on the substrate.

As shown in FIG. 1, the first silicon oxide based film A does not completely cover surface B of substrate C. It is believed that complete coverage cannot be achieved with the first silicon oxide based film because of surface shielding caused by foreign surface particles D. In effect, no silicon oxide based film is applied beneath the particles.

Therefore, before the second silicon oxide based film is applied, the shielding particles are removed and/or redistributed from the surface of the substrate with compressed gas. The compressed gas is most preferably air, nitrogen, argon or oxygen. The pressure of the gas is preferably at about 25 psi. Shielded regions E are exposed after the foreign surface particles are removed and/or redistributed with the compressed gas.

After the foreign surface particles are removed and/or redistributed with the compressed gas, the substrate is then again subjected to the glow discharge plasma process described above to deposit a second silicon based oxide film F and to produce a substantially pin hole free barrier coating on the substrate.

The deposition method of the present invention is preferably practiced at relatively high power and quite low pressure. A pressure less than about 100 microns Hg (0.1 Torr) should be maintained during the deposition, and preferably the chamber is at a pressure between about 43 to about 49 microns Hg during the deposition of film.

The substrate is electrically isolated from the deposition system (except for electrical contact with the plasma) and is at a temperature of less than about 80⌗C. during the depositing. That is, the substrate is not deliberately heated.

Figure 2:
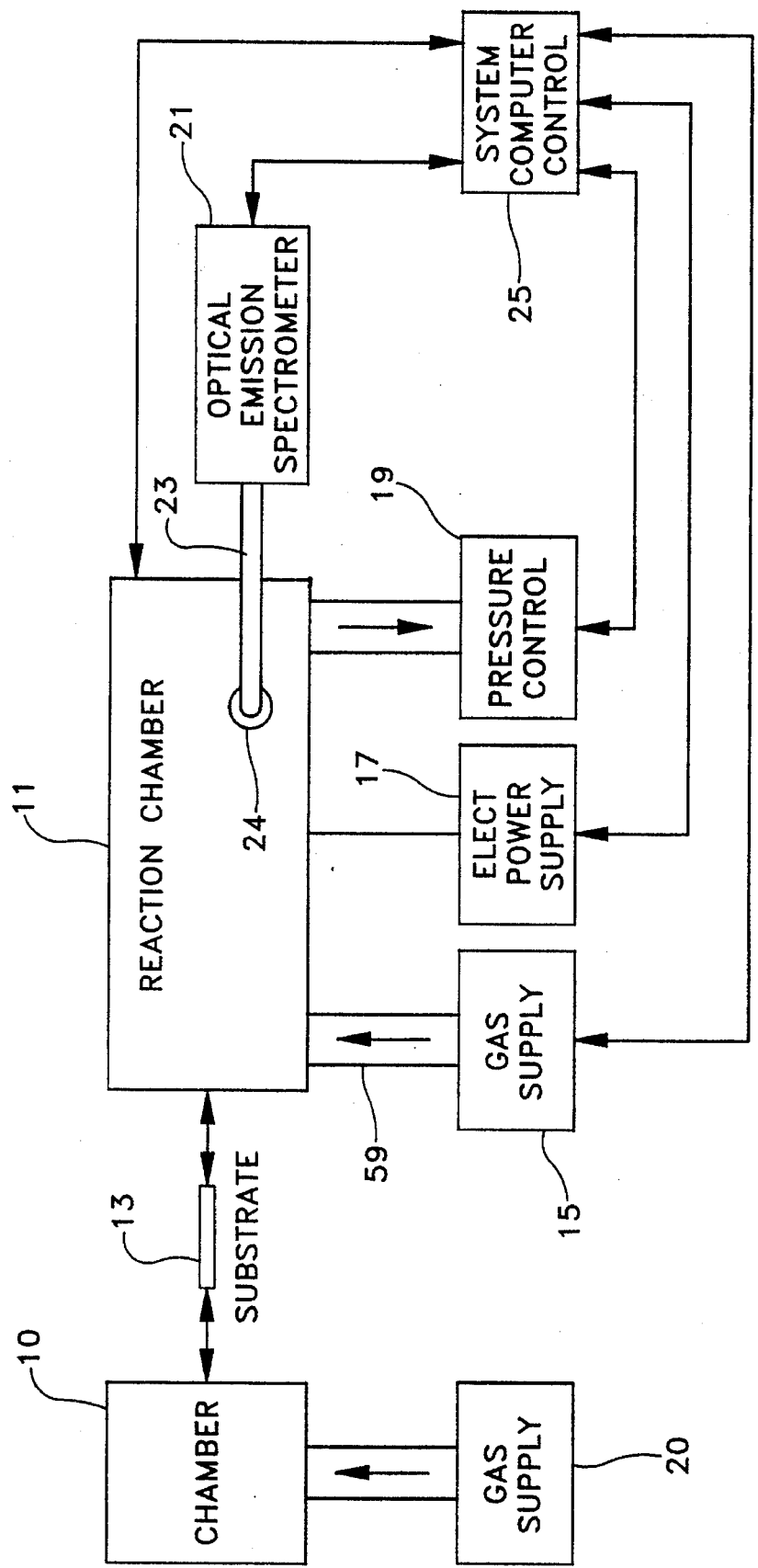
FIG. 2 is a general schematic diagram illustrating a plasma system utilizing the various aspects of the present invention.

Referring to FIG. 2, the system for sequentially depositing a silicon oxide based film and removing and/or redistributing surface particles is schematically illustrated. The system for depositing a silicon oxide based film comprises an enclosed reaction chamber 11 in which a plasma is formed and in which a substrate 13, is placed for depositing a thin film of material on it. The substrate can be any vacuum compatible material, such as plastic. One or more gases are supplied to the reaction chamber by a gas supply system 115. An electric field is created by a power supply 17, and a low pressure is maintained by a pressure control system 19. An optical emission spectrometer 21 is connected through an optical fiber light transmission medium 23 to the reaction chamber in some appropriate manner to couple the visible and near visible (especially the ultraviolet range) emission of the plasma to the spectrometer. A quartz window 24 in a side wall of the reaction chamber can be used to optically couple the plasma emission with external fiber medium 23. A general control system 25, including a computer control portion, is connected to each of the other components of the system in a manner to receive status information from and send controlling commands to them.

The reaction chamber can be of an appropriate type to perform any of the plasma-enhanced chemical vapor deposition (PECVD) or plasma polymerization process.

The system for removing and/or redistributing foreign surface particles includes an enclosed chamber 10 with a compressed gas supply system 20 for removing and/or redistributing the foreign surface particles that may be on the substrate.

Figure 3:
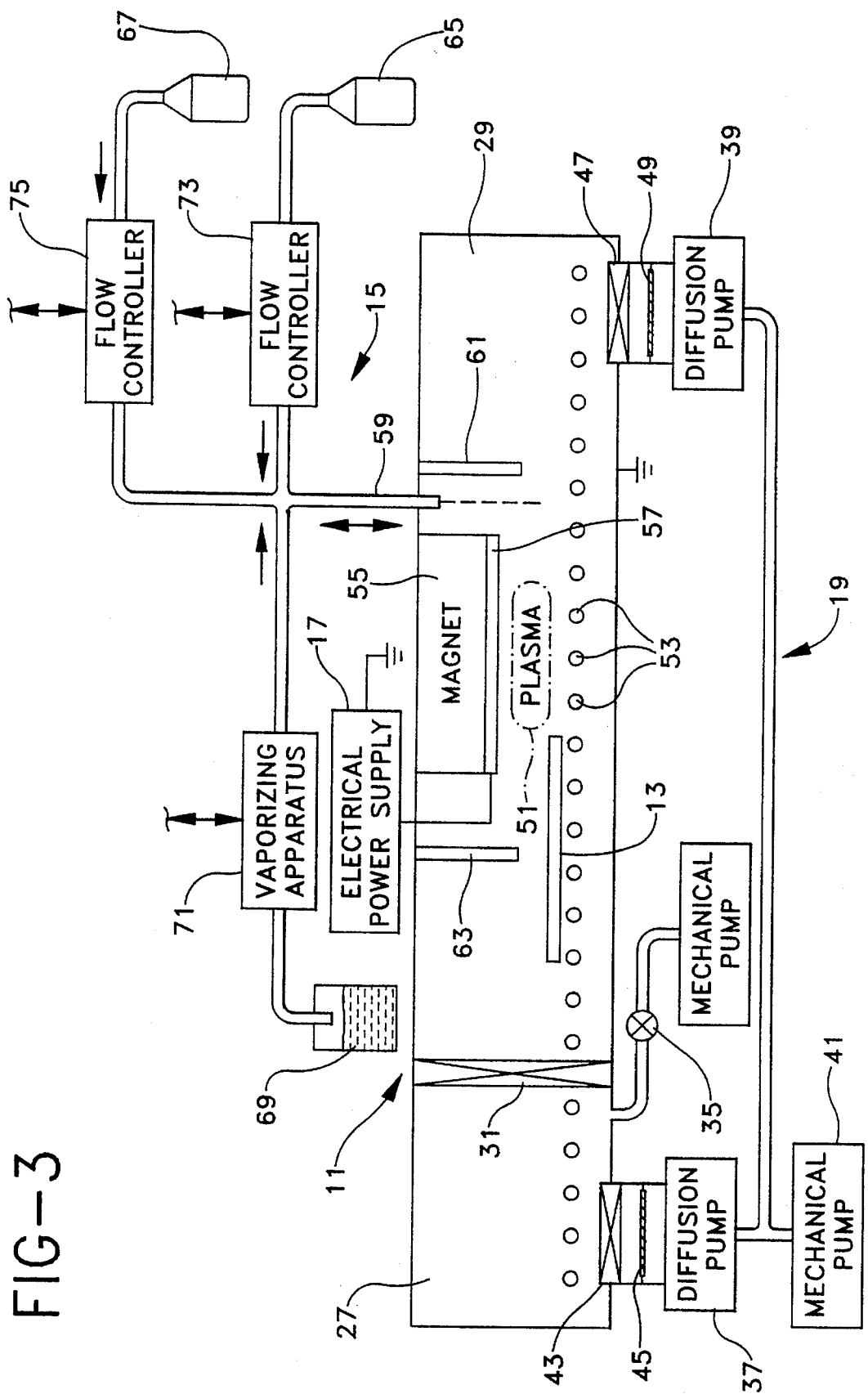
FIG. 3 is a schematic diagram illustrating a side sectional view of the plasma deposition chamber and its associated equipment as related to FIG. 2.

FIG. 3 shows a detailed side sectional schematic of the system of FIG. 2. In particular, reaction chamber 11 is divided into a load lock compartment 27 and a process compartment 29 by an isolation gate valve 31. Pressure control system 19 includes a mechanical pump 33 connected to load lock compartment 27 by a valve 35. The pressure control system also includes diffusion pumps 37 and 39, and an associated mechanical pump 41. Diffusion pump 37 is connected to load lock compartment 27 through an isolation gate valve 43 and an adjustable baffle 45. Similarly, diffusion pump 39 is connected to process compartment 29 through an isolation gate valve 47 and an adjustable baffle 49. Baffle 49 is controlled by system control 25, while a coating process is being carried out, in order to maintain the internal pressure at a desired value.

The substrate to be coated is first loaded into load lock compartment 27 with valve 31 closed. Mechanical pump 33 then reduces the pressure most of the way to the high vacuum region. Diffusion pump 37 is then operated to reduce the pressure further, to about $5 \times 10^{-2}$ Torr. The operating pressure is about 46 microns for a PECVD or plasma polymerization process and is achieved by flowing the process gases into the reaction chamber and throttling diffusion pump 39 using baffle 49. During loading and unloading operations, diffusion pump 39 maintains the deposition chamber 29 at the operating pressure. Once load lock compartment 27 is reduced to base pressure, valve 31 is opened and substrate la is moved into process compartment 29.

During the deposition process, substrate 13 is moved back and forth by means 53 through a plasma region 51, a number of times in order that the thin film deposited on the outer surface of the substrate has a desired uniform thickness.

A magnetron is positioned within chamber 29, formed of a magnetic structure 155 and a cathode 57. Power supply 17 has its output connected between cathode 57 and a metallic body of the reaction chamber. The magnetron creates an appropriate combination of magnetic and electrical fields in plasma region 51 in order to create a plasma there when the proper gases are introduced into the process compartment. The substrate is maintained electrically isolated and is passed directly through the plasma region.

The gaseous components necessary for the plasma to form in plasma region 51 are introduced into deposition chamber 29 by a conduit 59. Gas flows within deposition chamber 29 from diffusion pump 39. A pair of baffles 61 and 63 on either side of the magnetron help to confine the gas flow to plasma region 51.

After a first coating of the silicon oxide based film has been deposited on the substrate, the substrate is subjected to a stream of compressed gas at about 25 psi in chamber 10. Foreign surface particles on the substrate are removed and/or redistributed. The substrate is then returned to chamber 11 for a second coating of the silicon oxide based film.

Figure 4:
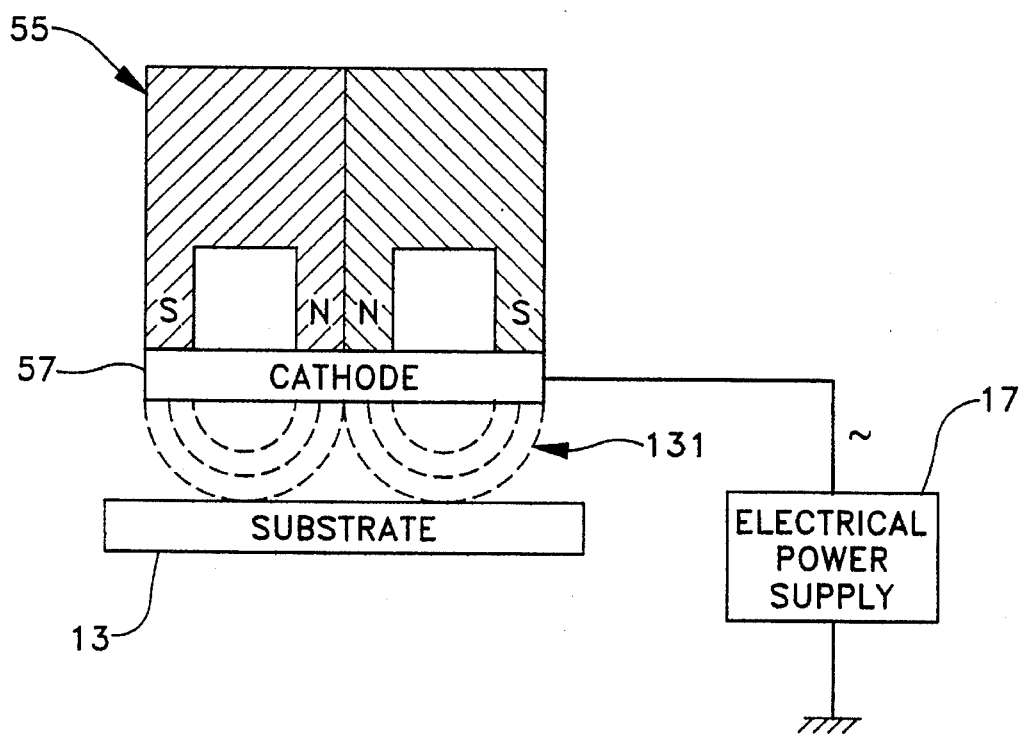
FIG. 4 illustrates the use of a balanced magnetron in the system of FIG. 3.

The magnetron used in process compartment 29 can be of a planar magnetron form as shown in FIG. 4. A cross-sectional view of the magnet structure 55 is provided at a vertical plane. In plan view, the structure of FIG. 4 is elongated in a direction normal to the plane of paper.

The structure of FIG. 4 is termed a balanced magnetron. Its magnetic lines of force 131 travel between one of the outer south magnetic poles and a central north pole. As is well known, electrons and ions travel in a spiral around a magnetic force line and along it, under influence of a combination of the magnetic field forces and the electric field forces formed by the cathode and the process chamber metal case. Cathode 57 is generally made of titanium or quartz, but sputtering is prevented from happening because of the higher pressure used in the deposition system of FIG. 3.

Figure 5:
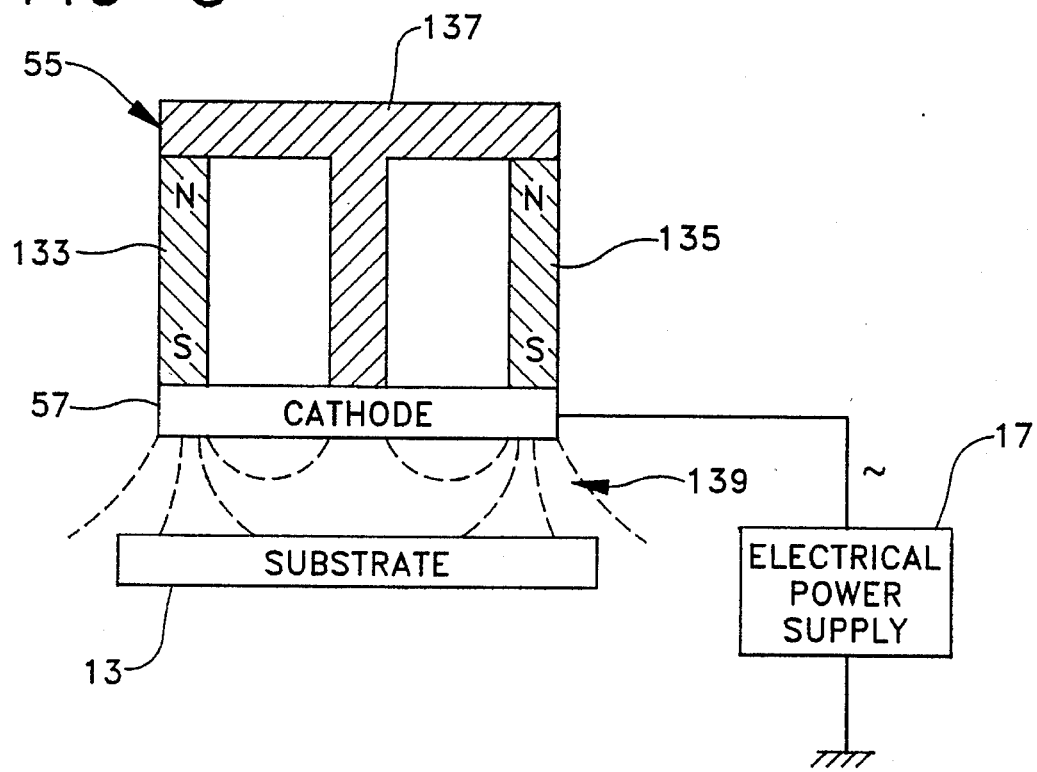
FIG. 5 illustrates the use of an unbalanced magnetron in the system of FIG. 3.

An unbalanced magnetron that alternatively can be utilized in the system of FIG. 3 is shown in FIG. 5. Outside magnets 133 and 135 are arranged with a soft iron core 137 middle. Only the south magnetic poles are positioned against a cathode 57, the north pole faces being oriented away from the cathode. The result is that a substantial proportion of the magnetic field line follow a much longer path in extending between the magnetic south and north pole regions.

The magnetron structures of FIGS. 4 and 5 are suitable for low frequency operation of power supply 17. An example frequency is 40 kHz. However, there can be some advantages from operating at a much high frequency, such as in the radio frequency range of several megahertz.

The silicon oxide based film or blends thereof used in accordance with this disclosure, may contain conventional additives and ingredients which do not adversely affect the properties of articles made therefrom.

Various other modifications will be apparent to and may be readily made by those skilled in the art without departing from the scope and spirit of the invention.

A variety of substrates can be coated with a barrier composition by the process of the present invention. Such substrates include, but are not limited to packaging, containers, bottles, jars, tubes and medical devices.

A variety of processes are also available in addition to plasma deposition for depositing a barrier composition. Such processes include, but are not limited to radio frequency discharge, direct or dual ion beam deposition, or sputtering.

The following examples are not limited to any specific embodiment of the invention, but are only exemplary.

EXAMPLE 1

METHOD FOR COATING A PLASTIC BLOOD COLLECTION TUBE WITH A SILICON OXIDE BASED FILM

An enclosed reaction chamber was evacuated to a base pressure of not greater than about $3 \times 10^{-6}$ Torr. The load lock was vented to atmosphere while the chamber was maintained under high vacuum. Then the load lock was evacuated with the plastic tube loaded therein. The chamber pressure was adjusted to a desired value by adjusting the baffle over the diffusion pump. The load lock diffusion pump was closed and the valve isolating the load lock and the chamber was opened. After the pressure in the chamber was stabilized, the power supply was turned on and adjusted to the desired value and a glow discharge plasma was established in the chamber. An emission spectrum from the control program was used to find the appropriate oxygen to inert gas ratio. The organosilicon flow into the chamber was then adjusted until the desired oxygen to inert gas ratio was obtained. The tube was then conveyed back and forth through the plasma region until the first coating thickness was achieved while continuing to monitor the process conditions. Once the first desired film thickness was obtained, the system was shut down and the coated tube was removed. The coated substrate was then placed in a second chamber with a compressed gas supply. The substrate was then subjected to the compressed gas to remove or redistribute the foreign surface particles. The substrate was then returned to the reaction chamber for a second coating of silicon oxide.

EXAMPLE 2

COMPARISON OF FILMS COATED AND UNCOATED WITH A SILICON OXIDE BASED FILM

The permeability of flat substrates made of polyethyleneterephthalate (PET), 1 mil in thickness with and without a silicon oxide based coatings were measured at 25° C.

The results of the oxygen transmission rates are given below:

| SAMPLE | Film Thickness (Å) | Oxygen Flux ($cm^3/m^2$ day atm) |
| --- | --- | --- |
| Uncoated PET film (1 mil) | 0 | 80 |
| $SiO_x$ on PET film without particle removal (1 deposition) | 500 | 35 |
| $SiO_x$ on PET film; vent chamber to atmosphere between depositions | 500 | 22 |
| $SiO_x$ on PET film; spray surfaces with carbon dioxide between depositions | 500 | 21 |
| $SiO_x$ on PET film; wipe surface with lint-free tissue between depositions | 500 | 7.5 |
| $SiO_x$ on PET film; wipe surface with a soft foam between depositions | 500 | 7.1 |
| $SiO_x$ on PET film; spray surface with helium between depositions | 500 | 4.6 |
| $SiO_x$ on PET film; spray surface with argon between depositions, | 500 | 2.0 |
| Same film after irradiation (10.5 Mrads) | | 0.5 |
| SiOx on PET film (AF power); spray surface with argon between depositions | 1750 | 0.5 |

All system parameters were kept essentially constant with the exception of the power source. A radio frequency (RF) power supply was used unless indicated differently.

The results show that a lower transmission rate is achieved by sequentially depositing $SiO_x$ with the intermittent removal and/or redistribution of surface particles with compressed gas, such as argon.

EXAMPLE 3

PROCEDURE FOR SEQUENTIAL PLASMA POLYMERIZATION OF TRIMETHYLSILANE/OXYGEN

A polymer substrate was cleaned in equal parts of a micro detergent and de-ionized (DI) water. The substrate was rinsed thoroughly in DI water and allowed to air dry. The cleaned substrate was then stored in a vacuum oven at room temperature until it was to be coated.

The cleaned substrate was then attached to a holder which fits midway between the electrodes in the glass vacuum chamber. The chamber was closed and a mechanical pump was used to achieve a base pressure of 5 mTorr.

The electrode configuration is internally capacitively coupled with permanent magnets on the backside of the titanium electrodes. The special configuration provides the ability to confine the glow between the electrodes because of the increase in collision probability between electrons and reacting gas molecules. The net result of applying a magnetic field is similar to increasing the power applied to the electrodes, but without the disadvantages of higher bombardment energies and increased substrate heating. The use of magnetron discharge allows operation in the low pressure region and a substantial increase in polymer deposition rate.

The monomer which consists of a mixture of trimethylsilane (TMS) and oxygen was introduced through stainless steel tubing near the electrodes. The gases were mixed in the monomer inlet line before introduction into the chamber. Flow rates were manually controlled by stainless steel metering valves. A power supply operating at an audio frequency of 40 kHz was used to supply power to the electrodes. The system parameters used for thin film deposition of plasma polymerized $TMS/O_2$ on the polymer substrate were as follows:

TMS Flow=0.75–1.0 sccm

Oxygen Flow=2.5=3.0 sccm

System Pressure=90–100 mTorr

Power=30 watts

Deposition Time=5 minutes

After the thin film was deposited, the reactor was allowed to cool. The reactor was then opened, and the sample holder is removed. The surface of the substrate was sprayed with a pressurized argon at approximately 25 psi. The mechanical action removes or redistributes the particles that may interfere with uniform film coverage. The sample was then immediately returned to the vacuum chamber. The chamber pressure was again reduced to approximately 5 mTorr and the deposition process described above was repeated.

What is claimed is:

1. A method of sequentially depositing a silicon oxide based film on a plastic substrate in a previously evacuated chamber by glow discharge comprising:

(a) placing a plastic substrate into a chamber;

(b) evacuating said chamber;

(c) controllably flowing oxygen into said chamber;

(d) establishing a glow discharge plasma in the chamber from said oxygen component;

(e) depositing a plasma of oxygen onto said plastic substrate;

(f) shutting down said chamber and evacuating;

(g) vaporizing an organosilicon component and admixing the volatilized organosilicon component with an oxidizer component and an inert gas component to form a gas stream exterior the chamber;

(h) controllably flowing the gas stream into the plasma;

(i) establishing a glow discharge plasma in the chamber from said gas stream;

(j) depositing a coating of silicon oxide on said plastic substrate;

(k) removing and/or redistributing foreign surface particles from said plastic substrate; and (l) repeating steps g through j above, thereby depositing another coating of silicon oxide on said plastic substrate.

2. The method of claim 1, wherein said oxidizer component is oxygen.

3. The method of claim 2, wherein the plastic substrate is electrically isolated from the chamber except for contact with the confined plasma.

4. The method of claim 3, further comprising magnetically confining at least a portion of the plasma adjacent to the substrate during the depositing.

5. The method of claim 4, wherein the organosilicon compound and oxygen of the gas stream being flowed into the plasma are in a flow rate ratio between about 1.2:1 to about 1:1.8 and the inert gas of the gas stream being flowed into the plasma is helium or argon in an amount effective to increase the deposition rate and the hardness of the deposited silicon oxide.

6. The method of claim 5, wherein the inert gas is helium in a ratio in the range from about 1:1.5 to 1:2.3.

7. The method of claim 1, wherein the organosilicon compound is 1,1,3,3-tetramethyldisiloxane, hexamethyldiallane, vinyltrimethylsilane, methyltri methoxyallane, vinyltrimethoxyallane or hexamethyldiallane or trimethylsilane.

8. The method of claim 1, wherein said plastic substrate is conveyed into and out of the plasma during the depositing.

9. The method of claim 1, wherein the inert gas is helium, the gas stream includes a minor amount of propylene, and the deposited silicon oxide based film includes carbon moieties.

10. The method of claim 1, wherein the gas stream includes a minor amount of nitrogen or nitrous oxide and the deposited silicon oxide based film includes nitrogen moieties.

11. The method according to claim 1, wherein said foreign surface particles are removed and/or redistributed with a pressurized gas stream.

12. The method of claim 11, wherein said pressurized gas stream of step (g) is nitrogen or argon at about 25 psi.

13. The method of claim 1, wherein said foreign surface particles are removed and/or redistributed with ultrasonic vibrations.

14. The method of claim 1, wherein said foreign surface particles are removed and/or redistributed by wiping said substrate.

15. A method of depositing a film on a plastic substrate by a plasma process in an evacuated chamber, comprising the steps of:

(a) placing a plastic substrate into a chamber;

(b) evacuating said chamber;

(c) controllably flowing oxygen stream into said chamber;

(d) establishing a glow discharge plasma in the chamber from said oxygen stream;

(e) depositing a plasma of oxygen onto said plastic substrate;

(f) shutting down said chamber and evacuating;

(g) providing said evacuated chamber with a gas stream that includes a source of a material desired to be deposited on said plastic substrate;

(h) establishing within said chamber a glow discharge plasma derived from the gas of said stream in a region of high electric field;

(i) removably positioning the plastic substrate in said plasma without any electrical connection therewith;

(j) generating within said plasma a magnetic field having a substantial magnetic flux directed against said plastic substrate, thereby depositing a first coating of a silicon oxide based film on said plastic substrate;

(k) removing and/or redistributing foreign surface particles from said plastic substrate; and (l) repeating steps (f) through (j) above, thereby depositing another coating of silicon oxide on said plastic substrate.

16. The method of claim 15, wherein the step of generating a magnetic flux includes positioning within said chamber a first magnetic pole oriented to face said plasma and a second magnetic pole oriented to face away from said plasma.

17. The method of claim 16, wherein the step of generating a magnetic flux includes positioning within said chamber a magnetic structure having a surface adjacent said plasma that is characterized by a magnetic flux distribution function in substantially any direction there across which varies from one magnetic strength of one polarity separated by a lesser magnetic strength of another polarity.

18. The method of claim 15, wherein the plasma is confined by means of an unbalanced magnetron.

19. The method of claim 15, wherein said foreign surface particles are removed and/or redistributed with a pressurized gas stream.

20. The method of claim 19, wherein said pressurized gas stream is nitrogen or argon at about 25 psi.

* * * * *